(12) United States Patent
Pagliarini et al.

(10) Patent No.: US 8,980,157 B2
(45) Date of Patent: Mar. 17, 2015

(54) METHOD AND APPARATUS FOR ASEPTIC MOULDING OF CONTAINERS OF PLASTIC MATERIAL

(75) Inventors: Paolo Pagliarini, Parma (IT); Matteo Di Prinzio, Guardiagrele (IT)

(73) Assignee: GEA Procomac S.p.A, Sala Baganza (IT)

( * ) Notice: Subject to any disclaimer, the term of this patent is extended or adjusted under 35 U.S.C. 154(b) by 462 days.

(21) Appl. No.: 13/522,644

(22) PCT Filed: Jun. 27, 2011

(86) PCT No.: PCT/IB2011/052821
§ 371 (c)(1),
(2), (4) Date: Jul. 17, 2012

(87) PCT Pub. No.: WO2012/007862
PCT Pub. Date: Jan. 19, 2012

(65) Prior Publication Data
US 2012/0292827 A1 Nov. 22, 2012

(30) Foreign Application Priority Data
Jul. 15, 2010 (IT) .............................. PR2010A0062

(51) Int. Cl.
| B29C 49/42 | (2006.01) |
| A61L 2/04 | (2006.01) |
| A61L 2/06 | (2006.01) |
| A61L 2/08 | (2006.01) |
| B29C 49/46 | (2006.01) |
| B29C 49/06 | (2006.01) |
| B29C 49/36 | (2006.01) |

(52) U.S. Cl.
CPC ............. *B29C 49/42* (2013.01); *B29C 49/4252* (2013.01); *A61L 2/04* (2013.01); *A61L 2/06* (2013.01); *A61L 2/082* (2013.01); *B29C 49/06* (2013.01); *B29C 49/36* (2013.01); *B29C 49/46* (2013.01)
USPC ........................ 264/454; 425/174.4

(58) Field of Classification Search
CPC .... B29C 49/42; B29C 49/4252; B29C 49/46; A61L 2/082
USPC ........................ 264/454; 425/174.4
See application file for complete search history.

(56) References Cited

U.S. PATENT DOCUMENTS

| 6,562,281 B1 | 5/2003 | Marchau et al. |
| 2009/0081326 A1 | 3/2009 | Adriansens et al. |
| 2009/0317506 A1 | 12/2009 | Adriansens |
| 2010/0054987 A1 | 3/2010 | Krueger |
| 2010/0089009 A1 | 4/2010 | Till |

FOREIGN PATENT DOCUMENTS

| DE | 10 2007 017938 A1 | 10/2008 |
| DE | 10 2007 050582 A1 | 4/2009 |
| EP | 0 996 530 A1 | 5/2000 |
| EP | 1 837 037 A1 | 9/2007 |
| EP | 1 896 329 | 3/2008 |

(Continued)

*Primary Examiner* — Alison Hindenlang
(74) *Attorney, Agent, or Firm* — Pearne & Gordon LLP

(57) ABSTRACT

Method for aseptic molding of containers (2) of plastic material, comprising the steps of: heating parisons (4) of plastic material; sterilizing the parisons (5) by means of soft X-rays inside an advancing tunnel (7) after heating them and before molding them; blowing the heated and sterilized parisons (4) in such a way as to obtain the containers.

6 Claims, 3 Drawing Sheets

(56) References Cited

FOREIGN PATENT DOCUMENTS

| | | |
|---|---|---|
| EP | 2 146 838 | 1/2010 |
| EP | 2 161 202 A1 | 3/2010 |
| FR | 2 907 684 A1 | 5/2008 |
| WO | 99/03667 A1 | 1/1999 |
| WO | 2006/136498 A1 | 12/2006 |
| WO | 2008/125216 A2 | 10/2008 |
| WO | 2009/052800 A1 | 4/2009 |

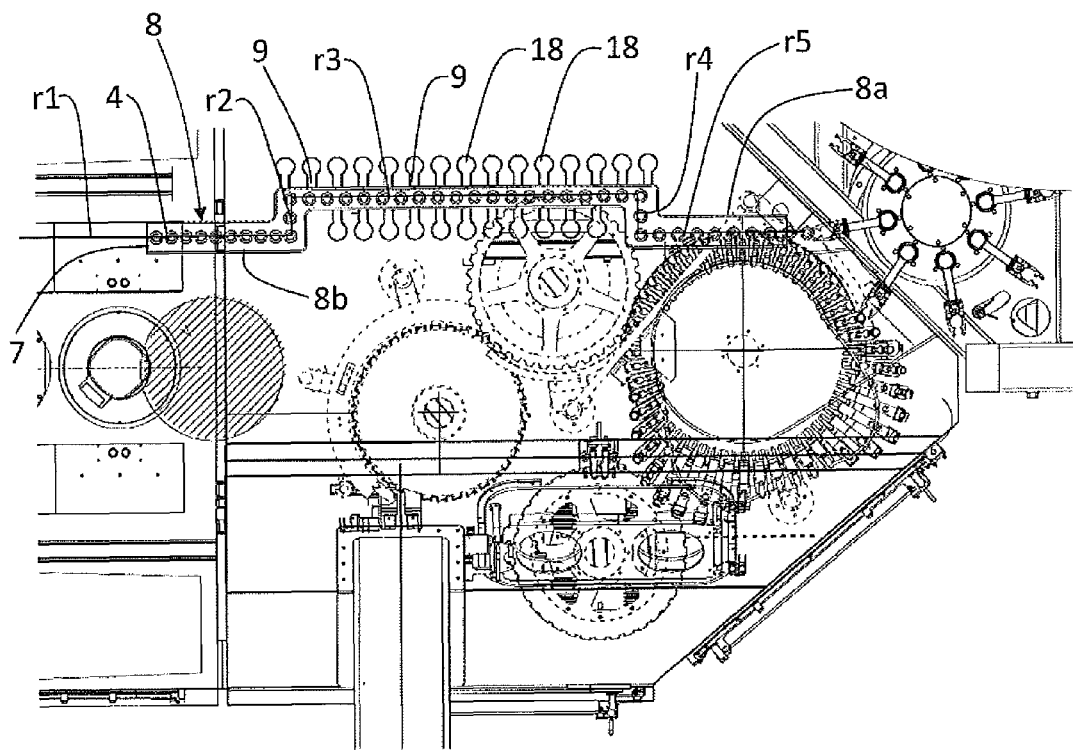
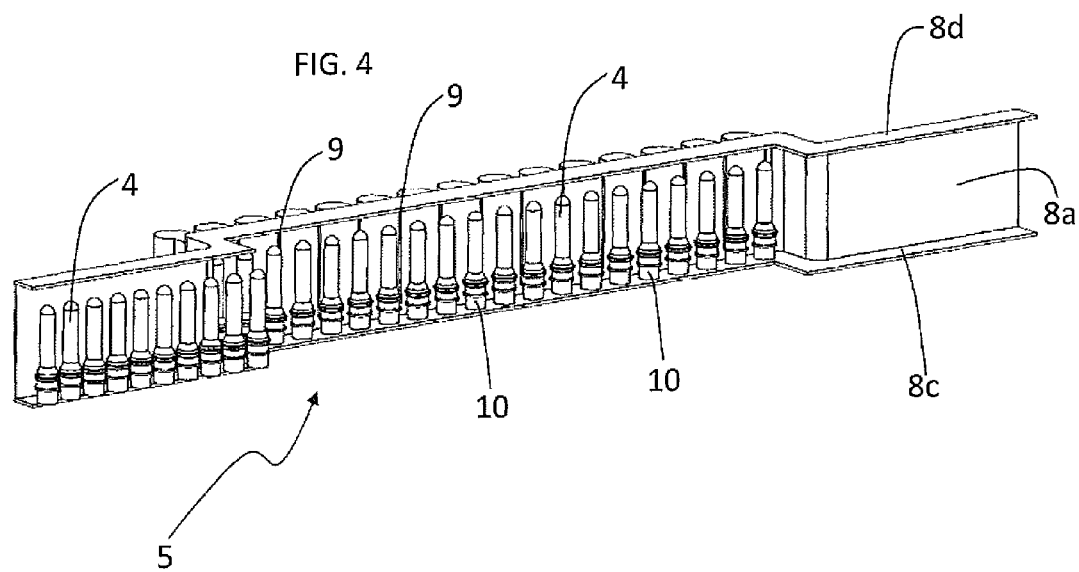

METHOD AND APPARATUS FOR ASEPTIC MOULDING OF CONTAINERS OF PLASTIC MATERIAL

TECHNICAL FIELD AND BACKGROUND ART

The present invention relates to a method and apparatus for aseptic moulding of containers of plastic material. As is well known, in an aseptic bottling line there exists a need to sterilize the moulded containers or parisons.

For example, document EP1837037 under the applicant's name proposed an apparatus and a method for chemically sterilizing the containers after the moulding step and before the filling step. However, sterilizing the parisons is preferable to sterilizing the moulded containers since the latter, having a larger surface area, require longer treatment times and, in the case of chemical sterilization, a greater consumption of sterilizing substances (e.g. hydrogen peroxide or peracetic acid).

In this respect, there is envisaged the possibility of sterilizing the parisons before sending them to the heating unit. However, such a solution poses the problem of having to deliver the parisons to the oven cold in order to obtain a correct temperature profile. Moreover, both the oven and the system for handling the parisons must be maintained sterile.

Another solution, proposed by document EP996530, envisages depositing a heat-activatable sterilizing substance (e.g. hydrogen peroxide) on the outer surface of the parisons. The parisons are subsequently conveyed to a heating unit where the sterilization thereof is completed. However, such a solution poses the following problems:
- the sterilization process must not interfere with correct pre-blow heating;
- the chemical residues deriving from sterilization must be disposed of;
- the processing times are lengthened.

Another solution, represented by document EP1896329, envisages moving the step of chemically sterilizing the parisons to after the heating thereof. However, this solution as well carries with it the disadvantages of using sterilizing chemical agents.

There also exists the possibility of using radiation sources to perform the sterilization, as described in document E22146838. Compared to chemical sterilization, radiation sterilization has the advantage of reducing the operating costs due to the consumption of chemical agents, it resolves the problem of disposing of chemical residues, and it enables the realization of eco-sustainable systems.

It may be noted, moreover, that radiation sterilization envisages the use, alternatively, of:
- directly ionizing radiation, such as electrons or other accelerated charged particles;
- indirectly ionizing radiation, such as X-rays or γ-rays;
- non-ionizing radiation, such as infrared rays, ultraviolet rays or visible light.

Low-energy directly ionizing radiation allows very high doses (several tens of kiloGrays) to be reached within a short time but has a limited capacity of penetration (only a few micrometers) into PET to be sterilized. On the other hand, indirectly ionizing radiation has a high capacity of penetration (several centimeters) into PET, but requires minutes or hours of time to reach the target sterilizing dose.

Among the prior art solutions, one may also note document FR2907684, in which the parisons are sterilized by means of infrared and ultraviolet rays. In this context, the technical task at the basis of the present invention is to propose a method and apparatus for aseptic moulding of containers of plastic material which overcome the drawbacks of the aforementioned prior art.

DISCLOSURE OF THE INVENTION

In particular, the object of the present invention is to propose a method for aseptic moulding of containers of plastic material which envisages preparing a step of sterilizing the parisons while simultaneously avoiding any lengthening of the overall processing times.

Another object of the present invention is to provide an apparatus for aseptic moulding of containers of plastic material which is also capable of sterilizing the parison while maintaining the overall dimensions practically unchanged.

The defined technical task and specified objects are substantially achieved by a method and apparatus for aseptic moulding of containers of plastic material, comprising the technical characteristics set forth in one or more of the appended claims.

BRIEF DESCRIPTION OF DRAWINGS

Further characteristics and advantages of the present invention will become more apparent from the approximate, and hence non-restrictive, description of a preferred, but not exclusive, embodiment of a method and apparatus for aseptic moulding of containers of plastic material as illustrated in the appended drawings, in which:

FIG. 3 illustrates a more detailed plan view of the enlarged portion of FIG. 2, in the first embodiment (the structure of the tunnel can be recognized);

FIG. 4 illustrates a perspective view of a detail (part of the tunnel) of the apparatus of FIG. 1, in the first embodiment;

BEST MODE FOR CARRYING OUT THE INVENTION

Figure 1:
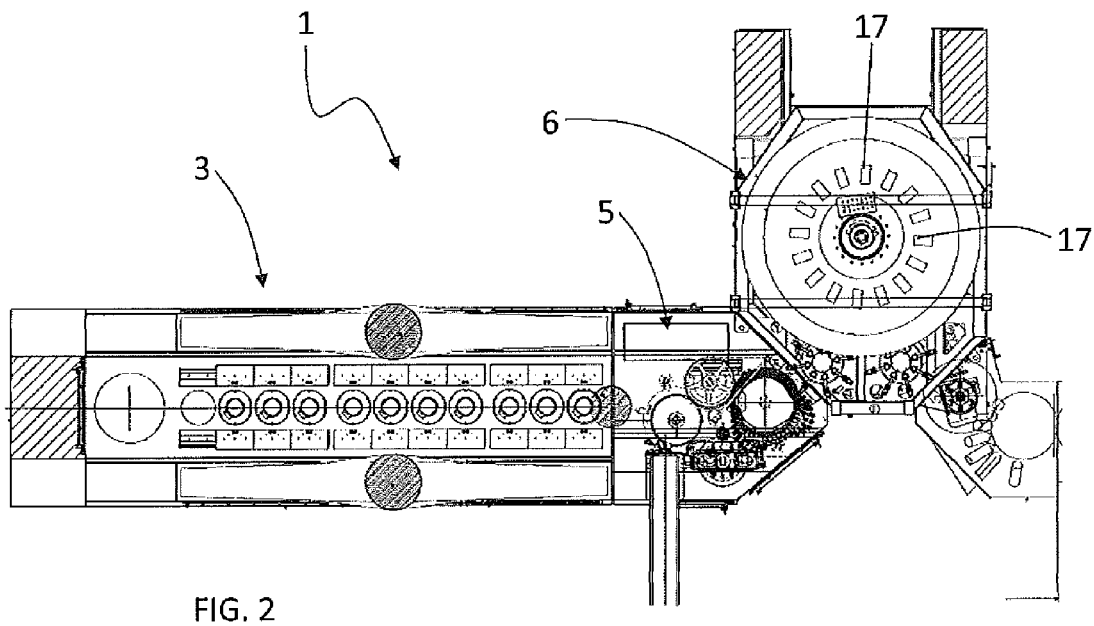
FIG. 1 illustrates a schematic plan view of a moulding apparatus according to the present invention.
Figure 2:
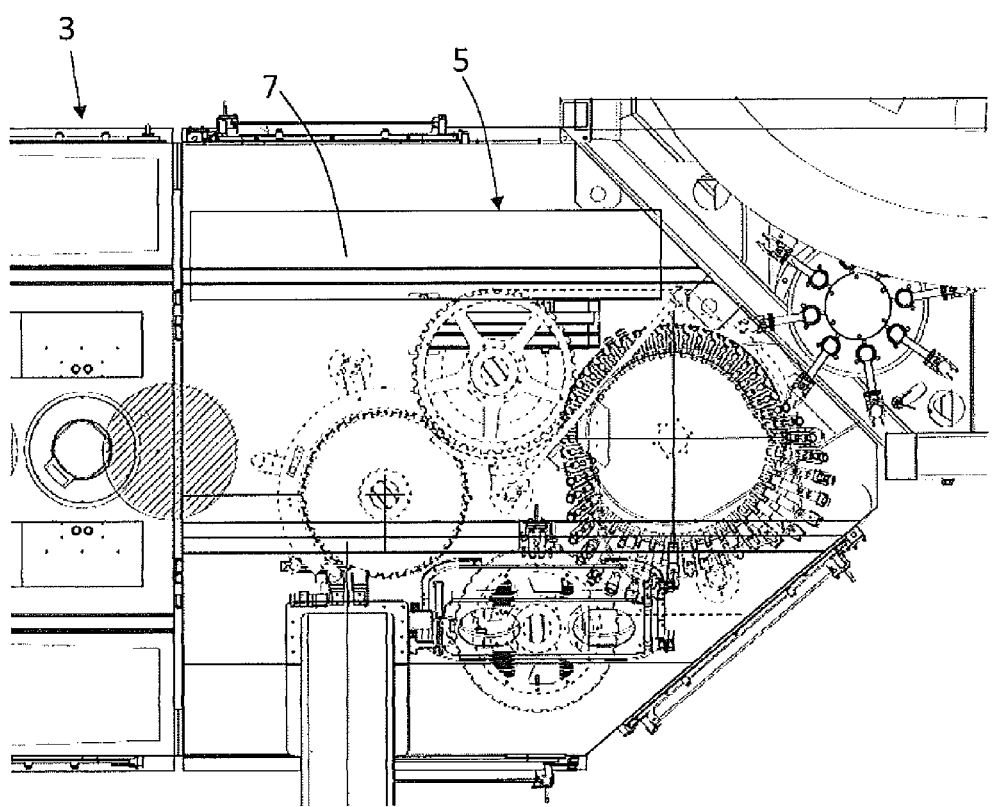
FIG. 2 illustrates a schematic plan view of an enlarged portion of the apparatus of FIG. 1, in a first embodiment.
Figure 5:
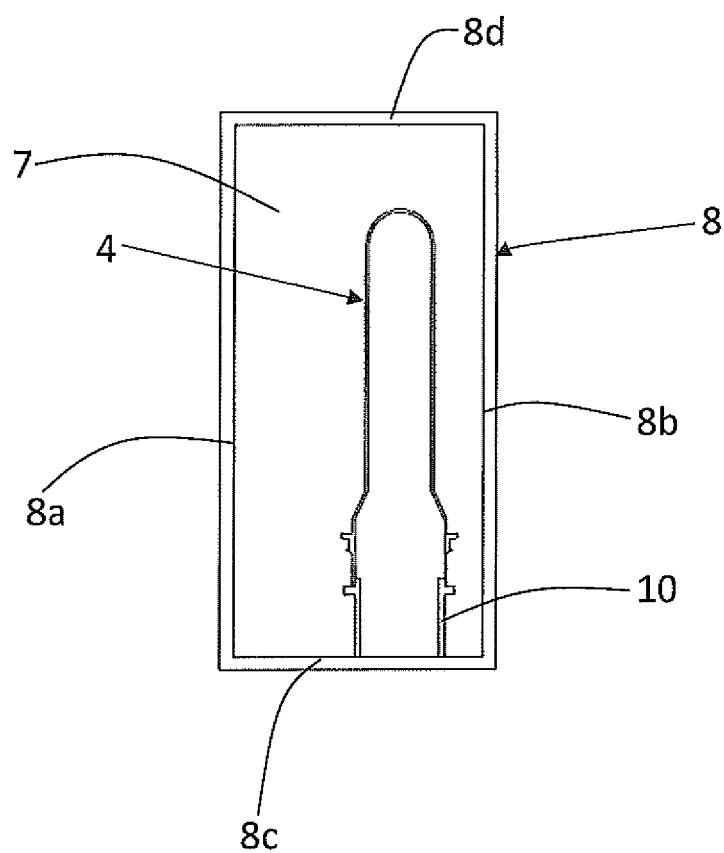
FIG. 5 illustrates a cross-sectional view of the tunnel of FIG. 4.

With reference to the figures, 1 indicates an apparatus for aseptic moulding of containers of plastic material, comprising:
- a unit 3 for heating parisons 4 of plastic material;
- a unit 5 for treating the parisons 4 by radiation;
- a unit 6 for blowing the heated parisons.

For example, the heating unit 3 includes a system of lamps such that the parisons 4 are heated by irradiation. As an alternative or in addition to the lamps, the heating takes place by forced convection of hot air. The heating unit 3 (or oven), having a linear configuration, is followed by the treatment unit 5.

The treatment unit 5 is interposed between the heating unit 3 and the blowing unit 6.

Originally, the treatment unit 5 comprises a tunnel 7 inside which the parisons 4 are made to move forward. Each parison 4 has its mouth supported by a respective support 10. Alternatively or additionally, each parison 4 is supported by grippers (not illustrated). The tunnel 7 is bounded by a shielding box-like body 8 having at least one opening 9 to allow the passage of radiation inside the tunnel 7.

The shielding box-like body 8, preferably having a layered structured of steel-lead-steel, comprises two lateral walls 8a, 8b, a bottom wall 8c and a top wall 8d. The opening 9 for the passage of radiation is obtained in one of the lateral walls 8a, 8b. Preferably, in the embodiment shown in FIG. 3, both lateral walls 8a, 8b have a series of narrow, elongated openings 9, i.e. veritable slits where radiation emitters 18 are active.

Advantageously, the tunnel 7 defines a path extending according to a simple broken line. In particular, said path extends from the end of the heating unit 3 towards the blowing unit 6. For example, in the embodiment described and illustrated in FIG. 3, the simple broken line is formed by:

a first straight line r1;
a second straight line r2 consecutive to the first straight line r1 and orthogonal thereto;
a third straight line r3 consecutive to the second straight line r2 and orthogonal thereto;
a fourth straight line r4 consecutive to the third straight line r3 and orthogonal thereto;
a fifth straight line r5 consecutive to the fourth straight line r4 and orthogonal thereto.

Originally, the radiation introduced into the tunnel 7 through the slits 9 are "soft X-rays". In particular, the soft X-rays can have energies below 60 keV.

The method for aseptic moulding of containers of plastic material according to the present invention is described below.

The parisons 4 are initially heated in the oven 3 so that on leaving the same they have a predefined thermal profile. Subsequently, the parisons 4 arrive at the treatment unit 5.

The parisons 4 move forward inside the tunnel 7 in such a way as to travel over the broken line defined by the succession of the first straight line r1, second straight line r2, third straight line r3, fourth straight line r4 and fifth straight line r5.

During their forward movement the parisons 4 are subjected to soft X-rays coming from the slits 9.

The sterilization treatment has a duration of between 10 and 15 seconds so as to enable completion of the thermal inversion of the heated parisons 4. The heated and sterilized parisons 4 then reach the blowing unit 6, which is made up of a plurality of blowing stations 17 where the heated (and sterilized) parisons 4 are blown in order to obtain the containers. The blowing unit 6 is of the rotary carousel (as illustrated in FIG. 1) or linear type.

The characteristics of the method and apparatus for aseptic moulding of containers of plastic material according to the present invention, are readily apparent from the description provided, as are the advantages thereof.

In particular, thanks to the fact that the sterilization of the parisons is performed by exploiting the time, traditionally idle, during which the parisons pass from the oven to the blower, it is possible to maintain the overall duration of the process practically unchanged. Furthermore, it is possible to reduce the dimensions of the sterile zone to a minimum.

Moreover, the use of soft X-rays represents a good compromise between capacity of penetration into the material and sterilization times. In fact, such radiation has energies below 60 keV, but is sufficient in any case to irradiate the entire thickness of the parisons in a substantially uniform manner. The X-ray generators can function continuously or produce high-intensity pulses lasting a few nanoseconds, which have a greater sterilizing capacity. Given that in order to obtain a pre-established level of sterilization with low-energy (less than 50 keV) radiation pulses it is necessary to use doses from 2 to 10 times smaller compared to treatment with high-energy (greater than 100 keV) ionizing radiation, the treatment time and power of the radiation generator can be reduced. As a result, it is possible to exploit the available time window for the passage of the parisons from the oven to the blower, equal to about 10-15 seconds, in order to perform a complete sterilization. The use of soft X-rays also requires less bulky and less costly shielding than is necessary if high-energy radiation is used.

The arrangement of the shielding tunnel has the advantage of avoiding any increase in the structural complexity and overall dimensions of the entire apparatus. Moreover, the shape of the tunnel prevents the radiation from reaching areas accessed by maintenance personnel.

Finally, the apparatus and method proposed avoid interfering in any substantial manner with the thermal profile of the parisons, which must complete inversion of the thermal gradient before the start of the blowing step.

The invention claimed is:

1. Method for aseptic moulding of containers (2) of plastic material, comprising the steps of:
heating parisons (4) of plastic material;
treating said parisons (4) by radiation;
blowing said heated and sterilized parisons (4) in such a way as to obtain the containers (2),
characterised in that the step of treating the parisons (4) is performed by sending soft X-rays inside an advancing tunnel (7) for the parisons (4) and takes place after the step of heating and before the step of blowing the parisons (4) themselves.

2. Method according to claim 1, wherein the step of treating the parisons (4) by radiation has a duration of between 5 and 15 seconds in order to enable completion of the thermal inversion of the heated parisons (4).

3. Apparatus (1) for aseptic moulding of containers of plastic material, comprising:
a unit (3) for heating parisons (4) of plastic material;
a unit (5) for treating said parisons (4) by radiation;
a unit (6) for blowing said heated parisons (4) comprising a plurality of blowing stations (17) in which the heated parisons (4) are blown to obtain said containers, said treatment unit (5) being interposed between the heating unit (3) and the blowing unit (6),
characterised in that said treatment unit (5) comprises a tunnel (7) inside which the parisons (4) are made to move forward, said tunnel (7) being bounded by a box-like shielding body (8) having at least one opening (9) to allow the passage of soft X-rays inside the tunnel (7).

4. Apparatus (1) according to claim 3, wherein said tunnel (7) defines a path extending according to a simple broken line.

5. Apparatus (1) according to claim 3, wherein said box-like shielding body (8) comprises two lateral walls (8a, 8b), said at least one opening (9) being obtained in one of said lateral walls (8a, 8b).

6. Apparatus (1) according to claim 5, wherein said tunnel (7) defines a path extending according to a simple broken line.

* * * * *